US008361394B2

(12) United States Patent
Resch-Genger et al.

(10) Patent No.: US 8,361,394 B2
(45) Date of Patent: *Jan. 29, 2013

(54) CALIBRATION SYSTEM AND DYE KIT AND THEIR USES FOR CHARACTERIZING LUMINESCENCE MEASUREMENT SYSTEMS

(75) Inventors: Ute Resch-Genger, Berlin (DE); Katrin Hoffmann, Berlin (DE); Dietmar Pfeifer, Berlin (DE); Roland Nitschke, Gundelfingen (DE); Pierre Nording, Gams SG (CH)

(73) Assignees: Bam Bundesanstalf Fuer Materialforschung und - Pruefung, Berlin (DE); Sigma-Aldrich GmbH, Buchs (CH)

( * ) Notice: Subject to any disclaimer, the term of this patent is extended or adjusted under 35 U.S.C. 154(b) by 704 days.

This patent is subject to a terminal disclaimer.

(21) Appl. No.: 11/378,966

(22) Filed: Mar. 17, 2006

(65) Prior Publication Data
US 2006/0233668 A1 Oct. 19, 2006

(30) Foreign Application Priority Data

Mar. 18, 2005 (DE) .......................... 10 2005 013 228
Oct. 11, 2005 (DE) .......................... 10 2005 049 365

(51) Int. Cl.
*G01N 21/76* (2006.01)
*G01N 21/64* (2006.01)
*G01N 21/00* (2006.01)
*G01N 31/22* (2006.01)
*G01N 31/00* (2006.01)
*B01L 3/00* (2006.01)

(52) U.S. Cl. ....... 422/82.08; 422/52; 422/402; 422/407; 422/82.05; 422/500; 436/19; 436/164; 436/172; 250/252.1

(58) Field of Classification Search ................ 422/50, 422/52, 55, 57, 58, 60, 61, 65, 82.05, 82.07, 422/82.08, 100; 436/19, 164, 172; 250/252.1, 250/458.1
See application file for complete search history.

(56) References Cited

U.S. PATENT DOCUMENTS
(Continued)

FOREIGN PATENT DOCUMENTS
DE    198 47 370 A1    4/2000
DE    102 00 865 A1   10/2002
(Continued)

OTHER PUBLICATIONS

U. Resch-Genger, et al.; "Traceability in Fluorometry: Part II. Spectral Fluorescence Standards"; Journal of Fluorescence, vol. 15, No. 3, May 2005, pp. 315-336.

(Continued)

*Primary Examiner* — Dean Kwak
(74) *Attorney, Agent, or Firm* — Norris McLaughlin & Marcus, P.A.

(57) ABSTRACT

A calibration system characterizes luminescence measurement systems, in particular spectrally resolving, wide-field and/or confocal imaging systems. The calibration system has a baseplate with at least one flow-through channel, wherein the at least one channel is formed as a sample chamber for the luminescence measurement system, at least one reservoir in communication with the at least one channel and adapted to receive a liquid, and at least one focusing device integrated into a baseplate for setting a defined measurement beam focus of the luminescence measurement system to be calibrated by using a focusing surface.

19 Claims, 2 Drawing Sheets

U.S. PATENT DOCUMENTS

| | | | |
|---|---|---|---|
| 5,689,110 | A | 11/1997 | Dietz et al. ............... 250/252.1 |
| 6,635,487 | B1 | 10/2003 | Lee et al. ........................ 436/19 |
| 6,911,344 | B1 * | 6/2005 | Reichert et al. ............... 436/518 |
| 2003/0030797 | A1 | 2/2003 | Palladino et al. .......... 356/243.1 |
| 2005/0232822 | A1 * | 10/2005 | Reed et al. ................... 422/100 |
| 2007/0211985 | A1 * | 9/2007 | Duer .............................. 385/12 |

FOREIGN PATENT DOCUMENTS

| | | |
|---|---|---|
| DE | 10 2004 044 717 A1 | 3/2006 |
| JP | 2000-159543 | 6/2000 |
| WO | WO 01/73417 | 10/2001 |
| WO | WO 03/029788 | 4/2003 |

OTHER PUBLICATIONS

U. Resch-Genger, et al.; "How to Improve Quality Assurance in Fluorometry: Fluorescence-Inherent Sources of Error and Suited Fluorescence Standards"; Journal of Fluorescence, vol. 15, No. 3, May 2005, pp. 337-362.

R. A. Velapoldi, et al.; Standard Reference Materials: A Fluorescence Standard Reference Material: Quinine Sulfate Dihydrate; U.S. Department of Commerce; National Bureau of Standards Special Publication 260-64; Jan. 1980.

Ambler Thompson, et al.; "Standards for Corrected Fluorescence Spectra"; Fluorescence Detection III, SPIE, Vlume 1054, 1989, pp. 20-25.

J.W. Hofstraat, et al.; "Correction of Fluorescence Spectra"; Applied Spectroscopy; vol. 48, No. 4, 1994, pp. 436-446.

J.A. Gardecki, et al.; "Set of Secondary Emission Standards for Calibration of the Spectral Responsivity in Emission Spectroscopy"; Applied Spectroscopy; vol. 52, No. 9, 1998, pp. 1179-1189.

Jean-Christophe Roulet, et al.; "Performance of an Integrated Microoptical System for Fluorescence Detection in Microfluidic Systems"; Analytical Chemistry, vol. 74, No. 14, Jul. 15, 2002, pp. 3400-3407.

* cited by examiner

CALIBRATION SYSTEM AND DYE KIT AND THEIR USES FOR CHARACTERIZING LUMINESCENCE MEASUREMENT SYSTEMS

The invention is relates to a calibration system for characterizing luminescence measurement systems, in particular spectrally resolving, wide-field and/or confocal imaging systems, a kit which includes the calibration system, and a dye set, as well as to uses of the system and the kit.

Each luminescence measurement technique supplies measurement data composed of contributions specific for the analyte and for the system. The undesirable system-specific contributions represent a wavelength and polarization dependence of system components of the employed measurement system. These dependencies are caused, in particular, by the optical components in the excitation and emission channel of the system, the excitation light source and the employed detection systems. These system-specific contributions have to be determined so as to be able to compare luminescence data across different systems and laboratories, to determine aging of the system, as a requirement for traceability of luminescence data to radiometric primary standards (according to the requirements of EN ISI/IEC 17025), as well as to draw quantitative conclusions about the fluorescence, to determine relative fluorescence quantum yields and to optimize luminescence methods. This applies particularly to comparative evaluations of wavelength-shifted luminescence profiles or to emission measurements at different excitation wavelengths. In addition, confocal spectral imaging systems require a determination of system parameters, such as the uniformity of the illumination, the spectral and spatial resolution (x, y, z) and the like. An important field of application for confocal microscopes with spectrally resolving detectors is the pixel-wise deconvolution of overlapping dye emissions in preparations having multiple fluorescence markers. No standard preparations are available to date to test robustness against interfering signals, such as poor signal-to-noise ratio, and to quantify the measurement accuracy at different concentrations.

Photoluminescence measurement systems include an excitation channel with, for example, an excitation light source and a wavelength-selective optical component, and an emission channel typically arranged perpendicular to the optical path of the excitation light, which is used to measure the light emitted by the fluorophore in the sample space after light absorption (photoluminescence). A certain portion of the excitation light is typically coupled to a reference channel through a beam splitter which includes an optical component, such as a mirror or a scatterer and a (reference) detector. The reference channel is used to record the actual excitation light intensity at the excitation wavelength for capturing temporary variations in the excitation light intensity. The aforementioned system-specific contributions to the fluorescence signal can be measured by determining so-called correction functions which describe the wavelength- and polarization-dependence of these effects in the emission and the excitation channel of the respective system. These correction functions are determined separately. The emission correction function includes the wavelength- and polarization-dependent transmission efficiency of the optical components in the emission channel and the wavelength- and polarization-dependent spectral sensitivity of the employed detection system. The excitation correction function describes the wavelength-dependent spectral radiance of the excitation light source and the wavelength- and polarization-dependent transmission efficiency of the optical components in the excitation channel.

The use of certified physical transfer standards for measuring system-specific effects is known. The excitation channel is typically calibrated with certified receiver standards, whereas the emission channel is calibrated with certified standard lamps. The use of physical transfer standards disadvantageously requires technical knowledge from the user in the field of optics, expensive recalibration, and is subject to changes in the spectral density due to the service life of the standard lamps. When standard lamps are used for emission correction, the different emission characteristics of lamp and sample and the difference in spectral radiance between the transfer normal and a typical luminescence sample must also be taken into account, which can be more than three orders of magnitude. All this can result in erroneous and unsatisfactory correction functions and is also complex and expensive. Most physical transfer standards are not suitable for calibrating simple, compact photoluminescence measurement systems.

So-called quantum counters are also used to measure the excitation correction. These are highly concentrated dye solutions which completely absorb light quanta and emit with a wavelength-independent fluorescence quantum yield. Quantum counters provide measurement data which depend on concentration and geometry and are also susceptive to polarization effects. Standardized calibration methods with defined concentrations in combination with defined measurement geometries are not available for quantum counters.

Also known are so-called fluorescence standards which are typically based on the photoluminescence of a chemical compound. Spectral fluorescence standards or so-called emission and excitation standards with known emission and excitation spectra, which have been corrected for system-specific effects, can be used to determine the spectral characteristics of photoluminescence measurement systems in the context of a system calibration. Such fluorescence standards are used in several forms, in particular in the form of solutions or embedded in solid polymer or glass matrices. Fluorescence standards have the advantage of having luminescence intensity and emission characteristics similar to those of the measured luminescence samples. Fluorescence standards can hence be used to spectrally calibrate under typical conditions encountered in sample measurements. Fluorescence standards can be measured in many different types of systems, formats and measurement geometries and are therefore suitable also for calibrating fluorescence measurement systems with special sample geometries or formats, for example micro-cuvettes, micro-titer plates and cryostat systems. Only fluorescence standards permit calibration in the same cuvette and measurement arrangement as the actual sample measurement and thus provide optimized calibration results. The problem with fluorescence standards is the large number of material and luminescence properties that must be determined. All application-relevant properties of a transfer standard must be fully characterized before it can be used, including the applied method and information about the measurement accuracy and adequate long-term stability in a solid pure state or in solution, for example embedded in a matrix.

The published literature discusses in detail certain recommendations for fluorescence standards, which also apply to emission and excitation standards and fluorescence quantum yield standards (e.g., U. Resch-Genger et al., J. Fluoresc. 2005, 15(3), 315ff; U. Resch-Genger et al., J. Fluoresc. 2005, 15(3), 337ff). However, quinine sulfate dihydrate (SRM936) is thus far the only emission standard where the corrected emission spectrum has been certified by a government institution, in this case by the National Institute for Standards and Technology (NIST, U.S.A.), with a traceable characterized reference fluorometer with a known measurement accuracy (R. A. Velapoldi, K. D. Mielenz, NBS Spec. Publ. 1980, 260-264, PB 80132046, Springfield, Va.). Only for this standard is information available about dye purity, the measurement parameters used to calibrate the employed spectrometer, and the measurement accuracy.

The spectral range where a fluorescence standard can be used for calibration is limited by the position and width of the fluorescence bands; if possible, only the bands with longest wavelength should be used for excitation standards. The emission standard quinine sulfate only covers, for example, the spectral range from approximately 400 to 550 nm. A combination of several chromophores with matched fluorescence spectra is required to calibrate a photoluminescence measurement system over the entire UV/vis/NIR spectral range. However, very few examples of standard combinations are known to date. Among those are, for example, combinations of emission standards, which consist of fluor-phosphor-containing polymer foils with NIST-certified emission spectra (A. Thompson, K. L. Eckerle, SPIE 1989, 1054, 20; J. W. Hofstraat & M. J. Latuhihin, Appl. Spectrosc. 1994, 48, 436). This system requires a defined measurement geometry, the use of polarizers and luminescence measurements in front-face-geometry, which makes it unsuitable for the calibration of simple measurement systems. The measurement conditions also deviate from those typical with liquid samples. Combining the various partial correction functions to a total correction function is not described.

Also known as emission and excitation standards are fluor phosphor-containing polymethylmethacrylate (PMMA) blocks in form of cuvettes. The used fluorophores typically have highly structured emission and excitation spectra with steep edges, so that the fluorescence profiles have a non-negligible dependence on the monochromator bandpass which worsens the calibration accuracy. Uncertainty about the wavelength accuracy can also cause large errors in the fluorescence intensity. The spectra are not traceable, they are not matched to each other, and they cannot be combined to a total correction function.

Other known dye solutions with different fluorophores frequently have a problem with narrow emission bands with steep edges and an insufficient spectral separation of absorption and emission bands, which makes them unsuitable as emission standards. Several substances have insufficient photo-stability and form under typical excitation and measurement conditions photoproducts with inherent spectral contributions. This applies in particular to their use in devices with high illumination intensity, in particular in laser-based measurement system and for confocal fluorescence microscopes. The low thermal and photochemical stability of most fluorescence standards designed for macroscopic applications limits their application for microscopes. The fluorescence anisotropy of many employed substances is too large and represents an additional error source during calibration and requires the use of polarizers. The produced spectra are mostly not traceable, information about the measurement accuracy is lacking and the spectra are certified by an authorized body only in exceptional cases (quinine sulfate dihydrate). Characterization of the application-relevant spectroscopic properties is frequently also incomplete, and information about the dye purity is often missing.

A statistic approach for combining two partial correction functions of the different dye standards to a total correction functions using a counting rate statistics (Poisson statistics) have been described by J. A. Gardecki and M. Maroncelli (Appl. Spectrosc. 1998, 52, 1179). The fluorescence standards employed therein still have some of the aforedescribed deficiencies, such as steep and structured bands ($\alpha$-NPO), insufficient photo stability in solution (tryptophane, coumarine 102) or an exceedingly high fluorescence anisotropy (LDS 751).

Not only are suitable dye standards for both spectral and quantitative calibration of photoluminescence measurement systems unavailable, but the system characterization of confocal spectral imaging systems is also difficult. In particular, different users may use different focus settings resulting in different probe depths in these measurements. This leads to poorly reproducible spectral effects replete with artifacts, caused by wall effects of the vessel and by the internal extinction effects in the dye. The exceedingly high excitation light intensities with laser excitation represent another problem in microscope systems, by accelerating the photo-chemical determination of the dye in the measurement volume, which can cause local "bleaching effects." A known container system with a micro-flow system for investigating chemical and biological samples with a light microscope and with spectroscopic tools is described, for example, in WO 029788 A2 which, however, does not solve the problem associated with non-reproducible focus settings and is also not intended for calibration purposes. U.S. Pat. No. 6,635,487 B1 discloses a device for calibrating fluorescence measurement systems with micro-fluidic sample chambers, which uses a solid fluorescence standard. The measurement beam is focused outside the sample by a slit. US 2003/0030797 A describes a device for calibrating fluorescence readout devices for micro-titer plates and proposes to use solid fluorescence standards in the form of cavities of the titer plates. The inserts include, for example, an optical quartz or glass body which ideally has a low inherent fluorescence and is coated with a fluorescence material, for example quinine sulfate. No focusing aid is provided.

It is therefore an object of the invention to provide a device for characterizing luminescence measurement systems, in particular spectrally resolving, confocal and/or wide-field imaging systems, which is easy to operate and provides a traceable and reproducible calibration by using standard solutions.

The object is solved by a calibration system with the features recited in claim 1. The calibration system according to the invention for characterizing luminescence measurement systems, in particular spectrally resolving, wide-field and/or confocal imaging systems, includes (a) a baseplate with at least one flow-through channel, wherein the at least one channel is formed as a sample chamber for the luminescence measurement system, (b) at least one reservoir in communication with the at least one channel and adapted to receive a liquid, and (c) at least one focusing device integrated into a baseplate for setting a defined measurement beam focus of the luminescence measurement system to be calibrated by using a focusing surface.

The at least one integrated focusing aid enables a reliable focus settings of the measurement beam (excitation beam) which is identical for all users, and thereby also makes it possible to measure essentially identically illuminated measurement volumes inside the micro-channels of the calibration device. In this way, spectral effects caused by different measurement depths, such as wall effects or interior filter effects of the solutions in the channels, can be minimized and standardized. As a result, reproducible measurement data are generated which can be compared and traced across different systems and different laboratories.

According to the preferred embodiments, at least two focusing devices (focusing aids) are provided and integrated in the baseplate. The two focusing devices are preferably distributed on the baseplate, in particular arranged on opposing marginal regions of the baseplate. The flatness or a deviation from the flatness can also be determined and compensated for the measurement locations of the calibration modules by numerical interpolation.

The focusing aid device can be implemented in different ways. The focusing device basically includes an almost ideally flat focusing plane with a roughness that is significantly less than the optical resolution of the luminescence measurement system to be calibrated. Preferably, the focusing device includes a substantially flat substrate, such as a wafer made of a silicon single crystal or the like, on which a very thin layer of a reflecting and/or fluorescing material is sputtered. This can be, for example, a thin metal layer (e.g., chromium layer) with a thickness between 10 and 100 nm, in particular between 30 and 50 nm. Alternatively or in addition, the focusing surface can be lumenescing, in particular fluorescing. Preferred in addition to the typical fluorescing materials are quantum dots which have a particularly high photo-thermal stability. Particularly advantageous are different fluorescing materials arranged on the same wafer or on different wafers with different spectral properties that cover the typical excitation or emission spectral range of the respective measurement system. The focusing device can then also be used to determine the parfocality (parfocality means that the specimen stays in focus when the objective is changed) of an employed objective of the measurement system, so that the parfocal image can be adjusted by computational methods or by using auxiliary lenses in the microscope.

The reservoirs, which in a particular embodiment include two reservoirs connected on both sides by a channel, provide excellent long-term stability, because molecules in the measurement volume which are disassociated by thermal and/or photo-chemical processes due to the high beam intensity at the sample location (laser excitation) typically employed in fluorescence microscopy, are continuously replaced from the reservoirs by diffusion processes. The volumes of the reservoirs and the dimensions of the channels are selected so as to provide adequate diffusion velocities. Moreover, the micro-flow system formed by the channel/reservoir unit can be completely sealed off from ambient air to prevent oxidation of the samples and evaporation of the employed solvent.

The dimensions (size of the baseplate, size and spacing of the (micro-) channels and focusing devices, size of the reservoir) and the material (glass, quartz glass, plastic) as well as the design and positioning of the focusing device(s) of the calibration system are adapted to the luminescence measurement system to be calibrated, for example to a spectrally resolving wide-field imaging system or a spectrally resolving confocal fluorescence microscope. For applications directed to calibrations of spectrally resolving, confocal fluorescence microscopes, the focusing aids can be integrated, for example on both sides of a calibration device having the typical dimensions of microscope slides, so that each user measures an almost identical illuminated volume. This allows a comparative and reproducible device characterization and thus also of measurement data under measurement conditions that are relevant for the application and specific to the samples.

According to a preferred embodiment of the invention, the at least one channel and/or the at least one reservoir associated with that channel are at least partially filled with a fluorescence standard. In another advantageous embodiment, the baseplate includes a plurality of channels with associated reservoirs, wherein the channels and/or the associated reservoirs are at least partially filled with different fluorescence standards.

In principle, the calibration system of the invention can be adapted to various applications and filled with different previously characterized dye solutions specifically selected for specific problems. Advantageously, the fluorescence standards can be selected so that their spectrally corrected fluorescence spectra in combination cover a predetermined spectral range with a predetermined minimum intensity and that numerical processing of the measured spectrum with the corresponding corrected, preferably certified spectra produces a total correction function that permits a calibration of the measurement system over a wide spectrum range. The total correction function is essentially determined by measuring the fluorescence spectra of the fluorescence standard, by computing the partial correction functions as a quotient of the measured and the respective corrected (ideally certified) fluorescence spectra, and by combining the partial correction functions to a total correction function using statistical methods. A particularly preferred method for computing a total correction function of this type as well as preferred sets of matched fluorescence standards are described in the prior application DE 10 2004 044 717.9.

Particularly preferred fluorescence standards for determining the relative spectral sensitivity of detection systems (emission or excitation) are matched to each other with respect to their different material properties and spectral characteristics in a manner described below. For example, a relative minimum intensity at the various intersecting wavelengths of any two spectrally adjacent fluorescence bands of two standards should be maintained. The minimum intensity is at least 20% of the maximum intensity of the bands, in particular at least 25%, preferably at least 30% of the maximum band intensity. In realistic exemplary embodiments, these intensities can even be approximately 40% of the maximum band intensity. The aforedescribed values refer to the UV/vis spectral range with $\lambda \leq 700$ nm. Because the quantum yields and absolute intensities are typically less in the NIR range with $\lambda > 700$ nm, smaller minimum intensities of at least 10%, in particular of approximately 15%, preferably approximately 25% of the maximum intensity of the respective flanking bands are permissible in this range at the intersecting points. This ensures that only high intensities enter the statistics for computing the total correction function for the measurement system to be calibrated, which results in a high reliability and low uncertainty. Based on the required minimum intensities, the matched fluorescence standards at least partially cover preferably a predetermined spectral range in the UV/vis/NIR range. In particular, a set of emission standards for emission correction covers a range of 310 to 730 nm, preferably from 300 to 950 nm, whereby a range of 400 to 800 nm is of particular relevance for microscopy applications. An advantageous set of excitation standards for excitation correction covers a range of 280 to 600 nm, preferably from 240 to 800 nm.

According to another advantageous embodiment of the invention, all fluorescence standards have fluorescence bands in the UV/vis spectral range with $\lambda \leq 700$ nm with a full width at half maximum ($FWHM_i$) of at least 1600 cm$^{-1}$, in particular of at least 2000 cm$^{-1}$, preferably of at least 2400 cm$^{-1}$, and in the NIR spectral range with $\lambda > 700$ nm of at least 1200 cm$^{-1}$, in particular at least 1400 cm$^{-1}$. The inventive composition of the kit(s) enables a user to reliably, reproducibly and inexpensively calibrate the measurement system. In particular, the inventive match of the various fluorescence standards, in particular of their half widths and the required minimum intensity at the intersecting wavelengths, makes it possible to generate a total correction function for the device over a wide spectral range with a quality that was unattainable to date.

In addition to the required minimum intensity of the fluorescence spectra at the intersecting points and the minimum half width, all fluorescence standards satisfy, according to additional embodiments of the invention, the following requirements. According to a particularly advantageous embodiment of the invention, all dye standards are selected so that their luminescence bands have a smoothest and unstructured curve shape, i.e., at a spectral resolution of 1 nm, the bands have only a single maximum, no shoulders and a continuous course. Like the required minimum half width which is associated with small slope at the band edges, the unstructured and smooth curve shape of the bands also guarantees optimal independence of the measured spectrum from the measurement conditions and device features, for example the parameters settings of the employed spectrometer, in particular of the monochromator bandpass and slit width of the measurement channel. The band characteristics according to the invention therefore increase the calibration reliability.

Moreover, all dye standards are provided with a purity of at least 98%, preferably of at least 99.5%. In addition, the overlap of the excitation and emission bands of each dye standards should be as small as possible. In particular, a preferred separation between excitation and emission bands is at least 2000 cm$^{-1}$, in particular of at least 2400 cm$^{-1}$, ideally at least 2800 cm$^{-1}$. In the temperature range of 20 to 30° C., the dye standards should also have a fluorescence anisotropy in the employed solvent in the UV/vis spectral range with $\lambda \leq 700$ nm of at most 0.05 and preferably of at most 0.04, in the NIR spectral range of at most 0.15 and preferably of at most 0.07. Other error sources in the calibration are eliminated in that the spectral shape of the fluorescence spectra of the proposed dye standards has only a small temperature dependence in a typical measurement temperature range of 20 to 30° C. The dyes are also characterized by a high thermal and photo-chemical stability of their pure starting materials and also of their solutions. Also important is the homogeneity of the standard solutions to guarantee position-independent fluorescence spectra up to the maximal spatial resolution of the measurement system. In addition, the dye standards are certain not to form photo products with inherent spectral contributions in the relevant spectral range in static photoluminescence measurements under a typical measurement and excitation conditions. In particular, the fluorescence bands decrease by maximally 10%, preferably maximally 2%, after 5-hour illumination with light from 150 Watt xenon high-pressure lamp in the region of the longest wavelength absorption maximum at a bandpass width of approximately 15 nm, so that the thermal and photo-chemical stability is sufficient for the planned applications. Conversely, should photo-chemical processes nevertheless occur, the reservoirs and the related diffusion processes replace the affected molecules in the measurement volume with undamaged dye molecules. In particular, the totality of the aforedescribed spectroscopic and chemical properties of the fluorescence standards provides a high calibration reliability and traceability to EN ISO/IEC 17025.

The calibration system can generally contain several different emission standards (and preferably their spectrally corrected emission spectra) for generating a total correction function for the emission channel (emission correction function) as well as several different excitation standards (and preferably their spectrally corrected excitation spectra) for generating a total correction function for the excitation channel (excitation correction function).

A set of preferred emission standards includes, in particular, compound selected from the group of biphenyl, naphthalene, coumarine, oxazin, merocyanin, hemicyanin and styryl derivates. Preferred excitation standards include derivates from the group containing biphenyl, naphthalene, coumarine, oxazin, merocyanin, hemicyanin and styryl derivates. Several explicit emission and/or excitation standards, which satisfy the aforedescribed criteria, are listed below.

A first preferred emission and/or excitation standard is a biphenyl derivate having the general formula 1

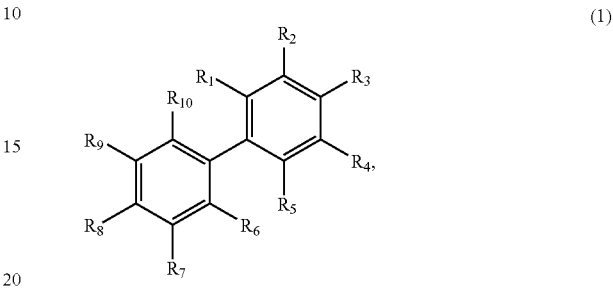

(1)

Wherein $R_1$ to $R_{10}$ independently represent a hydrogen group, an alkyl or alkoxy group, or partially in combination with each other an anellated, saturated hetero- or homo-nuclear ring. Preferably, $R_1$ and $R_6$ each represent an alkoxy group and the other groups independent of each other a hydrogen or alkyl group. The alkoxy or alkyl groups are independent from each other cyclic or acyclic, branched or linear. In a particular preferred embodiment, $R_1$ and $R_6$ each represent a methoxy group and the other groups each a hydrogen group. This compound is preferably used as emission standard and has, for example, in ethanol an emission band of 290 to 410 nm at an excitation wavelength of 280 nm. The half width is approximately 4250 cm$^{-1}$ and the separation between excitation and emission maximum approximately 5410 cm$^{-1}$.

A second preferred emission and/or excitation standard is a naphthalene derivate having the general formula 2

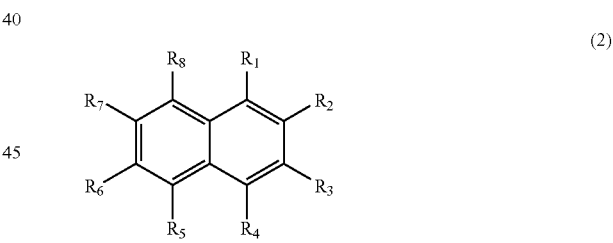

(2)

wherein $R_1$ to $R_8$ independently represent a hydrogen or alkoxy group, or partially in combination with each other an anellated, saturated hetero- or homo-nuclear ring. Preferably, at least one of the two naphthalene rings is substituted with two mirror-symmetrically arranged alkoxy groups (for example, $R_1$ and $R_4$ and/or $R_2$ and $R_3$), with the remaining groups being hydrogen. The alkoxy groups are acyclic, branched or linear and do not have hydrogen groups in β-position relative to the ether oxygen atom. In a particular preferred embodiment, $R_1$ and $R_4$ represent independently from each other a methoxy or neopentyloxy group, and the other groups are each hydrogen groups. These compounds are preferably used as emission standards and have, for example, in ethanol an emission band of 330 to 500 nm at an excitation wavelength of 320 nm. The half width is approximately 4400 cm$^{-1}$ and the separation between excitation and emission maximum approximately 4930 cm$^{-1}$.

A third preferred emission and/or excitation standard is a coumarine derivate having the general formula 3

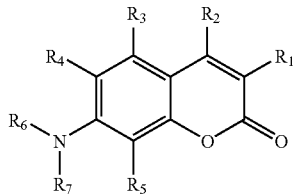
(3)

wherein $R_1$ to $R_7$ independently represent a hydrogen or an unsubstituted or a substituted alkyl group, or partially in combination with each other an anellated, saturated homonuclear ring. In particular, $R_1$ and $R_2$ represent independent of each other a hydrogen or an unsubstituted or a substituted alkyl group or an anellated, saturated homo-nuclear ring. $R_3$ to $R_5$ represent a hydrogen group and $R_6$ and $R_7$ independently a hydrogen or alkyl group. Preferably, $R_1$ to $R_5$ are each a hydrogen group and $R_6$ and $R_7$ each an ethyl group. This compound is used as emission and/or excitation standard and has, for example, in ethanol an emission band at approximately 400 to 600 nm at an excitation wavelength of 380 nm, and an excitation band of 325 to 430 nm at a detection wavelength of 460 nm. The half width of the emission band is approximately $2850\ cm^{-1}$ and the separation between excitation and emission maxima approximately $4340\ cm^{-1}$. The excitation band has a half width of approximately $3780\ cm^{-1}$.

A fourth preferred emission and/or excitation standard is a coumarine derivate having the general formula 4

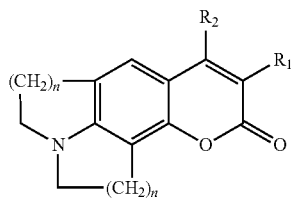
(4)

wherein $R_1$ and $R_2$ independently represent a hydrogen or an unsubstituted or a substituted alkyl group, or in combination with each other an anellated, saturated homo-nuclear ring, and n is equal to 1 or 2. $R_1$ preferably represents hydrogen, $R_2$ an unsubstituted or a substituted alkyl group, and n is equal to 1 or 2. Particularly preferred is $R_1$ hydrogen, $R_2$ a trifluormethyl group and n equal to 2. This compound is used as emission and/or excitation standard and has, for example, in ethanol an emission band at approximately 460 to 700 nm at an excitation wavelength of 420 nm, and an excitation band of 330 to 490 nm at a detection wavelength of 530 nm. The half width of the emission band is approximately $2890\ cm^{-1}$ and the separation between excitation and emission maxima approximately $4940\ cm^{-1}$. The excitation band has a half width of approximately $4010\ cm^{-1}$.

A fifth emission and/or excitation standard is an oxazin derivate, in particular a 3H-phnoxazine-5-on derivate, having the general formula 5

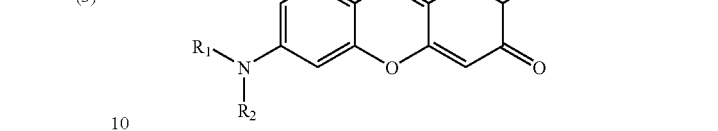
(5)

wherein $R_1$ and $R_2$ independently represent a hydrogen or an unsubstituted or a substituted n- or iso-alkyl group. $R_1$ and $R_2$ are preferably an unsubstituted, linear alkyl group, in particular and ethyl group. The compound is used as emission and/or excitation standard and has, for example, in ethanol an emission band at approximately 570 to 750 run at an excitation wavelength of 550 nm, and an excitation band of 440 to 630 nm at a detection wavelength of 630 nm. The half width of the emission band is approximately $1630\ cm^{-1}$ and the separation between excitation and emission maximum approximately $2440\ cm^{-1}$. The excitation band has a half width of approximately $2960\ cm^{-1}$.

A sixth emission and/or excitation standard is a merocyanin derivate having the general formula 6

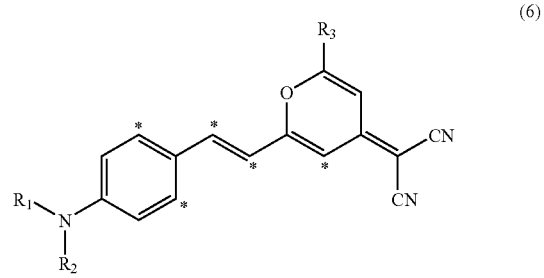
(6)

wherein $R_1$, $R_2$ and $R_3$ independently represent a hydrogen or an unsubstituted or a substituted n- or iso-alkyl group, and an unsubstituted or a substituted alkyl group. The C-atoms labeled with an asterisk can be bridged independently by a saturated C2 or C3 bridge, if they are in relative 1,3 position. Preferably, $R_1$, to $R_3$ are each a methyl group, without any bridging. This compound is preferably used as an emission standard and has, for example, in ethanol an emission band at approximately 530 to 750 nm at an excitation wavelength of 460 nm. The half width of the emission band in acetone is approximately $2323\ cm^{-1}$ and the separation between excitation maximum ($\lambda_{ex}$=462 nm) and emission maximum ($\lambda_{max}$=626 nm) approximately $5670\ cm^{-1}$.

Another emission and/or excitation standard is a styryl derivate, in particular a hemicyanin derivate, having the general formula 7

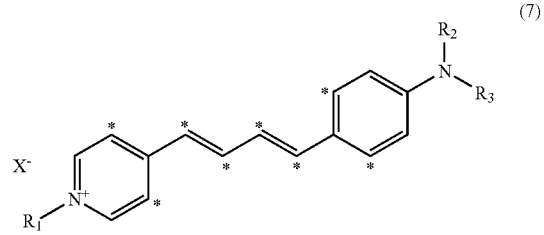
(7)

wherein $R_1$ to $R_3$ independently represent a hydrogen or an unsubstituted or a substituted n- or iso-alkyl group, and $X^-$ an unspecified anion. The C-atoms labeled with an asterisk can be bridged independently by a saturated C2 or C3 bridge, if they are in relative 1,3 position. Preferably, $R_1$ is an ethyl group, $R_2$ and $R_3$ are each a methyl group, and $X^-$ a perchlorate anion. No bridging ring exists. This compound is preferably used as emission standard and has an emission band at approximately 600 to 800 nm at an excitation wavelength of 500 nm. The half width of the emission band in acetone is approximately 2008 cm$^{-1}$ and the separation between excitation maximum ($\lambda_{ex}$=492 nm) and emission maximum ($\lambda_{max}$=719 nm) approximately 6417 cm$^{-1}$.

Another emission and/or excitation standard is a styryl derivate, in particular a hemicyanin derivate, having the general formula 8

(8)

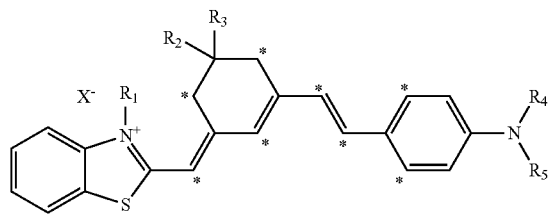

wherein the groups $R_1$ to $R_5$ independently represent a hydrogen or an unsubstituted or a substituted n- or iso-alkyl group, and $X^-$ an unspecified anion. The C-atoms labeled with an asterisk can be bridged independently by a saturated C2 or C3 bridge, if they are in relative 1,3 position. Preferably, $R_1$ to $R_5$ are each a methyl group, and $X^-$ a perchlorate anion. The compound is preferably used as emission standard and has an emission band at approximately 700 to 920 nm at an excitation wavelength of 580 nm. The half width of the emission band in acetone is approximately 1460 cm$^{-1}$ and the separation between excitation maximum ($\lambda_{ex}$=564 nm) and emission maximum ($\lambda_{max}$=810 nm) approximately 5380 cm$^{-1}$.

Another preferred emission and/or excitation standard is a p-terphenyl having the general formula 9

(9)

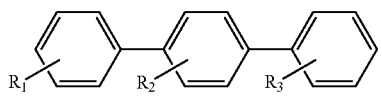

wherein $R_1$ to $R_3$ independently represent a hydrogen or an alkyl or alkoxy group, preferably hydrogen. The compound is preferably used as excitation standard and has, for example in ethanol, an excitation band at approximately 240 to 320 nm if the fluorescence is detected at 335 nm. The half width of the excitation band is 5580 cm$^{-1}$.

Another preferred emission and/or excitation standard is a 1,3,4-oxadiazol derivate having the general formula 10

(10)

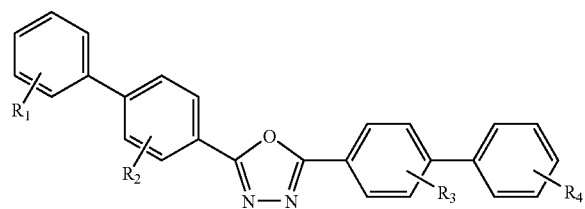

wherein $R_1$ to $R_4$ independently represent a hydrogen or an alkyl or alkoxy group, preferably each hydrogen. The compound is preferably used as excitation standard and has, for example in acetonitrile, an excitation band at approximately 275 to 350 nm and an emission maximum around 373 nm. The half width of the excitation band is 4880 cm$^{-1}$.

A calibration system according to a particularly preferred embodiments includes a set of emission standards, with each standard including a fluorescence standard according to the general formulas 1 to 5. Such set covers the spectral range from approximately 310 to 730 nm. The set can include for the emission channel at least one additional emission standards selected for the general formulas 6, 7 and 8, which allows a determination of a total correction function for a range from approximately 310 to 950 nm.

A particularly preferred calibration system for generating a total correction function for the excitation channel includes a set of excitation standards, which each includes a respective excitation standard according to the general formulas 3, 4, 5, 9 and 10.

Another aspect of the invention relates to a kit with an (unfilled) calibration system of the invention, as described above, and a set of different fluorescence standards either in solution or as a solid. Preferably, the set of fluorescence standards has the aforedescribed properties and is selected from the aforedescribed materials. According to another preferred embodiment, the kit also includes corrected fluorescence spectra of the fluorescence standards included in the kit in the computer-readable form and/or information about an Internet page, from which the corrected fluorescence spectra can be recalled. The kit advantageously also includes a program algorithm for computing a total correction function for a predetermined spectral range and/or information about an Internet page from which the program can be recalled. A suitable algorithm is described, for example, in the prior application DE 10 2004 044 717.9. The kit according to the invention enables a user to comfortably and easily calibrate the measurement system by following instructions in an operating manual.

The calibration system of the invention and/or the kit are preferably used for a relative spectral calibration of photoluminescence measurement devices, in particular for determining to system-specific spectral contributions to the measurement data. The calibration system and/or the kit can also be used as a fluorescence quantum yield standard for determining relative fluorescence quantum yields in the UV/vis/NIR spectral range, i.e., for a quantitative calibration of the intensities. The fluorescence quantum yield is defined as the ratio of the photons emitted by a sample to the number of photons absorbed by the sample. The kit and the fluorescence standards may also be used for determining the linearity region of a detection system of a photoluminescence measurement system. In this case, the region of a detector is determined where the intensity indicated by the detector increases linearly with the received intensity, which makes possible a reliable a quantitative statement about the concentration of a chromophore in the sample. The channels of the calibration system are here filled with different concentrations of the same fluorescence standard. The calibration system can also be used to characterize the long-term stability and day-to-day instrument performance variations of the measurement intensities of the measurement system, as well as to compare different luminescence measurement systems with each other. Additional applications may include, for example, the characterization of the uniformity of the elimination at different excitation and emission wavelengths, the ability to compare luminescence data and intensities, the determination of relative spectral radiance at the sample location and spectral deconvolution and checking of evaluation software used for these purposes.

Depending on the format, size and arrangement of the channel structures, the calibration system can be used for characterizing various types of photoluminescence measurement systems, for example confocal spectrally resolving imaging systems, such as confocal fluorescence microscopes and micro-array scanners, wide-field fluorescence microscopes, as well as Raman spectrometers and Raman microscopes. The calibration system can be used for different measurement geometries. Further adaptation to the problem is possible by selection of the dyes and dye combinations, for example adapted for system-specific excitation wavelengths and detectable emission spectral regions, as well as different signal levels and fluorescence intensities or intensity ratios. The calibration system of the invention is intended for use by trained technical personnel.

The features of additional preferred embodiments of the invention are recited in the depended claims.

Exemplary embodiments of the invention will be described in detail with reference to the corresponding drawings.

Figure 1A:
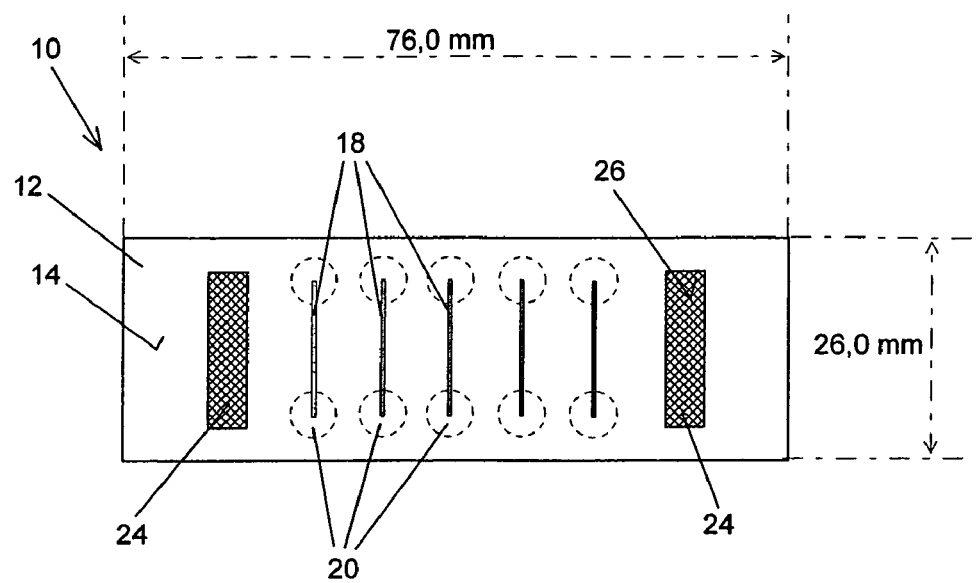
FIG. 1A shows a bottom view of a calibration system according to the invention.
Figure 1B:
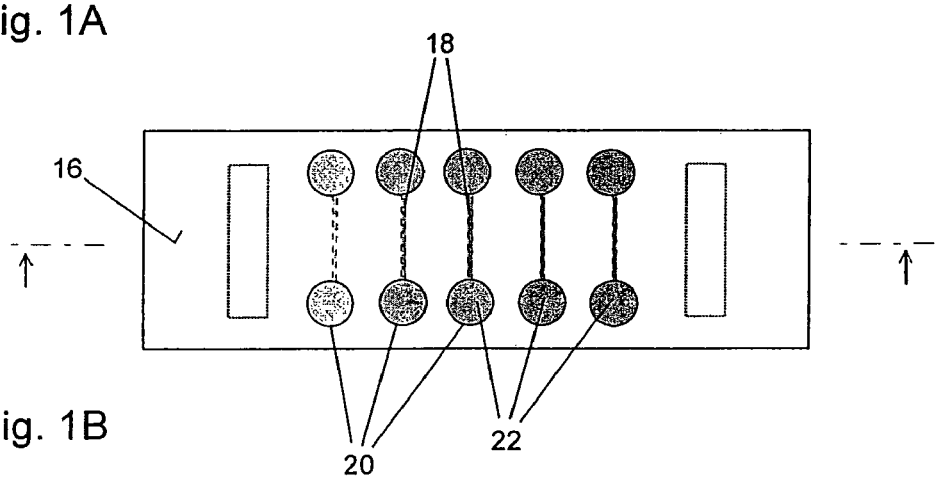
FIG. 1B shows a top view of the calibration system of FIG. 1A according to the invention.

FIGS. 1A and 1B show different views of a calibration system indicated with a reference symbol 10 according to an advantageous embodiment of the invention for calibrating, in particular, a confocal fluorescence microscope. The calibration system 10 includes a two-dimensional baseplate 12 with a bottom side 14 and a topside 16. The baseplate can be made of a suitable polymer, glass or quartz glass, and can be made in one-piece or in several pieces from different materials. The dimensions of the baseplate 12 in the depicted example are 76.0 mm×26.0 mm and hence correspond to standard dimensions of object holders for microscopes.

The calibration system 10 has several (in the present example five) channels 18 which extend through the baseplate 12 parallel to the bottom side and topside 14, 16 and to the lateral edges of the baseplate 12 and are arranged with a defined equidistal mutual spacing. The channels 18 extend close to the surface of the baseplate that faces of the measurement beam of the luminescence measurement system to be calibrated, in this case the bottom side 14. The channels 18 may also be machined into the baseplate 12 as grooves and covered with an optically transparent foil which can be glued or welded to the baseplate 12. As clearly seen in FIG. 1D, the channels 18 exit on both sides of surface 6 of the baseplate 12, terminating in reservoirs 20. Accordingly, two reservoirs 20 arranged on the topside 16 of the baseplate 12 are associated with each channel. The reservoirs 20 can be formed as hollow cylinders and the like. The reservoirs 20 can be sealed against ambient air, for example with externally applied covers (not shown).

The interior spaces of the channels 18 form the actual sample or measurement chambers of the luminescence measurement system, i.e., for measuring the luminescence characteristic of a sample disposed in a channel 18, the measurement beam is focused in the interior spaces of the channel 18. The channels 18 have preferably a rectangular cross-section (FIG. 1C), for example with a height of the 0.4 mm, a width of 3.8 mm, and a length of 17.0 mm. The diameters of the (micro-) channels 18 and the size of the reservoir are selected so that new dye molecules reach the measurement location through diffusion processes to replace molecules destroyed or damaged by photochemical and thermal processes.

The channels 18 and the reservoirs 20 in communication with these channels are filled with solutions of different fluorescence dye standards 22, as indicated in the figures by the different gray levels of the solutions. The liquid columns of two respective reservoirs 20 form a system that hydrostatically communicates via a channel 18. The fluorescence standards 22 includes, for example, a set of matched emission standards for calibrating the emission channel of the measurement system or matched excitation standards for calibrating the excitation channel of the system. The properties of the preferred fluorescence standards 22 will be described in the context of FIG. 2.

Figure 1C:
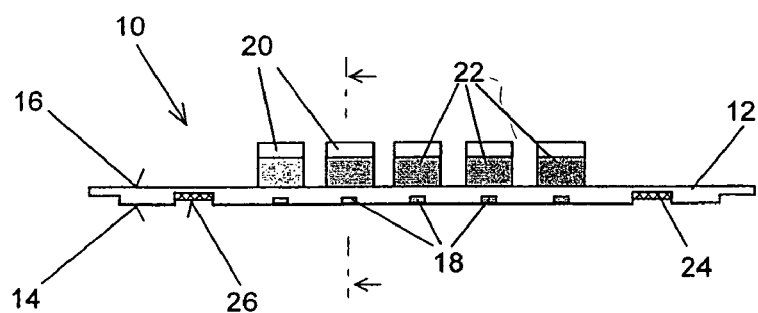
FIG. 1C shows a longitudinal cross-section of the calibration system according to the invention along the intersection line indicated in FIG. 1B.
Figure 1D:
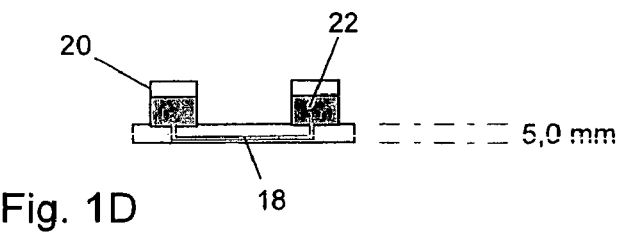
FIG. 1D shows a cross-section of the calibration system according to the invention along the intersection line indicated in FIG. 1C.

Two focusing devices 24, which in a preferred embodiment are arranged at opposite marginal regions of the baseplate 12, are inserted in corresponding recesses of the bottom side 14 of the baseplate 12. However, different from the depicted embodiment, more than two focusing devices 24 can also be distributed on the baseplate 12, or only a single focusing device may be used. If only a single focusing device 24 is used, this device is advantageously arranged in the center region of the baseplate 12. The focusing devices 24 each have a focusing surface 26 extending parallel to the channels 18 and aligned with the interior spaces of the channels 18 (FIG. 1C). In other words, the focusing surfaces 26 are in the same plane as the channels 18, in particular as the radial centers of the channels 18.

In the depicted example, the focusing devices 24 are implemented as highly planar wafers made of silicon single crystals which have a respective reflecting focusing surface 26. The focusing surface 26 consists of a thin layer of chromium sputtered onto the wafer which forms the substrate. The chromium layer has a layer thickness of 40 nm. The roughness of the focusing surface is significantly less than the optical resolution of the luminescence microscope to be calibrated. Other wafer materials or reflecting metal layers are also feasible. Alternatively, the focusing devices 24 can also include highly planar lumenescing focusing surfaces 26. These can be implemented, for example, as very thin layers of fluorescing semiconductor nanoparticles, so-called quantum dots, consisting of several hundred to several thousand atoms, which are deposited on a silicon wafer or the like by, for example, spin sputtering. Known fluorescing materials for quantum dots are, for example, cadmium-selenide, cadmium-telluride, indium-phosphide, lead-selenide, and others. Optionally, the quantum dots can be coated with a cover layer. Compared to conventional fluorescing material, quantum dots are advantageously very stable and resist bleaching. The layer thickness of the fluorescing focusing surface 26 preferably corresponds to a mono-layer of quantum dots and is therefore in a range of, for example, 7 to 10 nm. In other fluorescing or reflecting substances, the layer thickness is preferably only a few atomic or molecular layers of the respective material, preferably mono-atomic.

The illustrated calibration system 10 is designed for an inverted fluorescence microscope, where the excitation beam is incident on the measurement volume from below, i.e., from the bottom side 14 of the baseplate 12. However, the calibration system of the invention can also be designed for fluorescence microscopes where the excitation beam is incidental on the object from above. In this case, the micro-channels 18 are located on the same side as the focusing devices 24 and the reservoirs 20. The number of channels 18 can also vary and/or they can be arranged differently, for example the channels 18 can extend along the baseplate 12.

The fluorescence microscope is focused with the focusing devices 24 according to the invention in the following manner. The calibration system 10 is first positioned on a microscope stage of the fluorescence microscope. The measurement beam (excitation beam) of the system is then moved with the microscope stage, which can be adjusted with a motor in three dimensions, to one of the focusing devices 24 in the x, y-direction. (Alternatively, depending on the design of the microscope, the excitation beam can also be moved to the desired measurement location of the system by the adjustable optics while the fixed microscope stage remains fixed). The beam is then focused exactly on the focusing surface 26 of the focusing device 24 in the z-direction by moving the microscope stage with a motor in the z-direction (or the optics of the microscope is adjusted accordingly). The position is then determined where the maximum reflection signal (or fluorescence signal for a fluorescing focusing surface 22) is detected. This process can be performed completely automatically. The detected focus setting is stored as z-coordinate, or as frontal separation between the sample (focusing surface 22) and the front lens of the optics. If several focusing devices 24 are used, the same process is employed with the other focusing devices 24. Different focus settings (z-coordinates or frontal separations) for the different focusing devices 24 imply that the baseplate 12 is not entirely flat. The z-coordinates for the x, y-positions of the channels 18 arranged between the focusing devices 24 can then be numerically interpolated. The fluorescence standards contained in the channels are then measured. The measurement beam is sequentially moved to the channels 18 and focused according to the respective stored or interpolated z-coordinate in the interior of the channel. The measurements in the channels need not be performed at exactly the height of the focusing surfaces 26, but can also be performed at different depth, for example a depth that is different by 30 μm. In this case, the optical focus is adjusted relative to the zero-setting for the respective channel 18 by this depth. The determination of the focus with the focusing devices 20 serves therefore as a reference value for the respective channels 18. In this case, the integrated focusing devices 24 ensure that the same sample volume is measured in each channel 18. Spectral effects caused by different measurement depths in the modules 24, such as wall and internal filter effects, can then be standardized across devices and laboratory boundaries, thereby producing comparable and traceable measurement and calibration results.

The further process for calibrating the system based on preferred fluorescence standards 22, which together with the calibration system 10 and the corrected fluorescence spectra a digital form are part of an inventive kit, will now be described.

In the present example, a set of five fluorescence standards 22 (emission standards) A, B, C, D and E are used for calibrating the emission channel of a fluorescence microscope, wherein A is a biphenyl derivate, B is a naphthalene derivate, C and D are each coumarine derivates, and E is an oxazin derivate. In an actual example, these are represented by the following dyes:

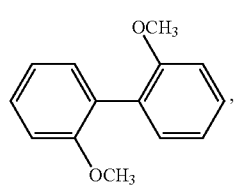

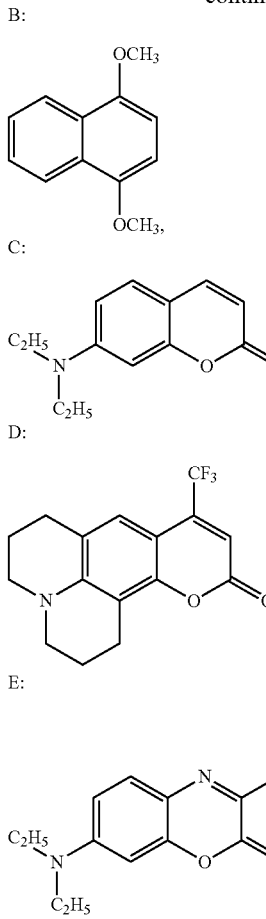

Figure 2:
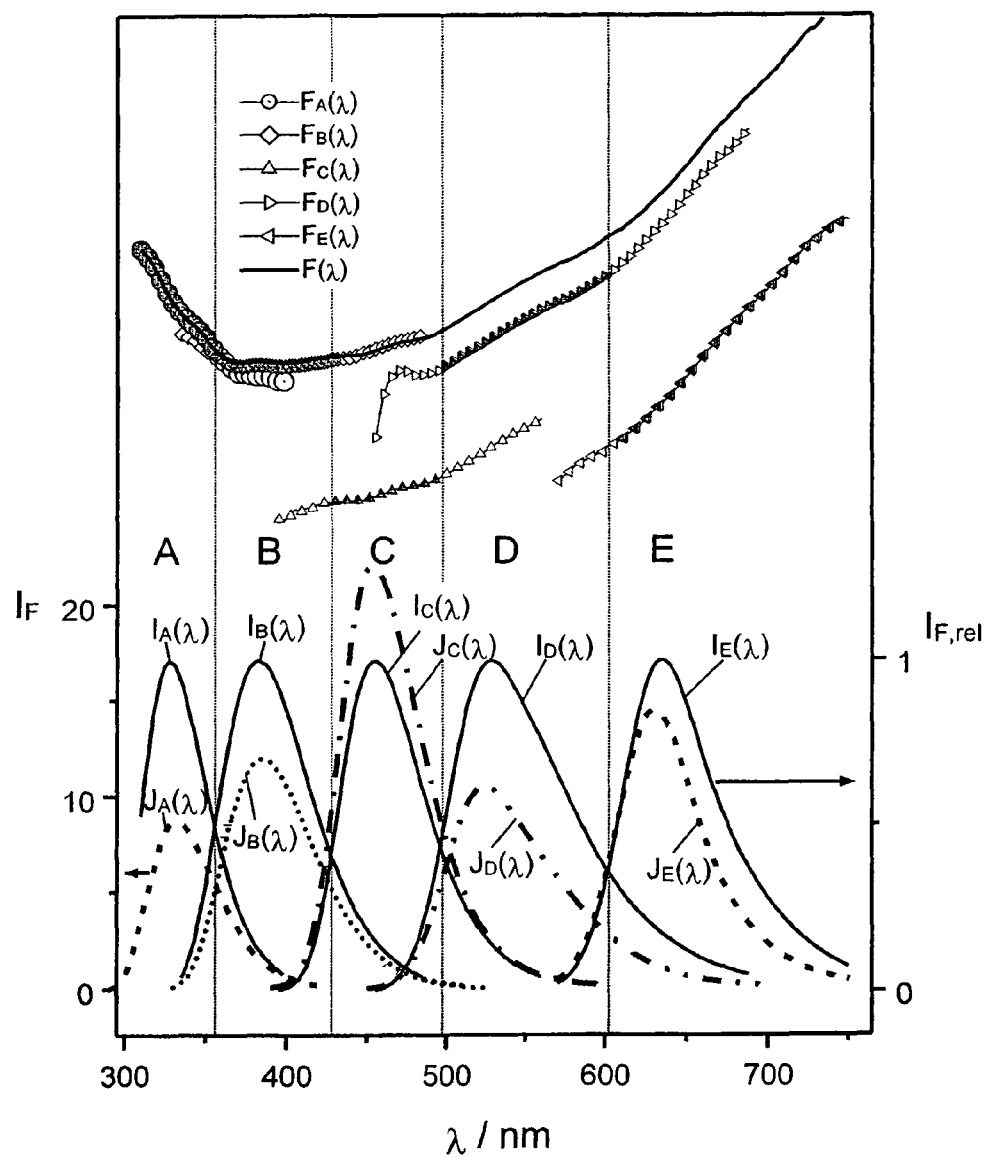
FIG. 2 shows corrected (certified) and measured emission spectra of dye standards A to E and computed partial correction functions and a total correction function.

All dyes have a purity of better than 99%, and have long-term stability in particular in solid form in the presence of oxygen from ambient air, when stored in the dark at 4° C. The air-saturated solutions have sufficient long-term stability when stored in the dark at 4° C., and under measurement and excitation conditions typical for photoluminescence measurements do not form photoproducts, which absorb or to emit in the spectral range used for calibration. The lower section of FIG. 2 shows the spectrally corrected and normalized emission spectra of the emission standards A to E $I_A(\lambda)$ to $I_E(\lambda)$ (continuous lines). As can be seen, the standards spectra all have each broad and unstructured bands with only a single maximum and no shoulders or discontinuities in the spectral range used for calibration. The fluorescence dyes are also carefully selected for large wavelength separations between the maximum of the emission spectra and the associated absorption spectra (not shown) (Stokes shift) to eliminate reabsorption of emitted photons due to the overlap between emission and absorption bands. This separation is, in particular, for the dyes A, B, C, D and E approximately 5400, 4900, 4300, 4900 and 2400 $cm^{-1}$, respectively. The dyes also have a small anisotropy with r≦0.05 (UV/vis spectral range with λ≦700 nm) and a sufficiently small temperature dependence of the shape of the fluorescence bands in the temperature range between 20° C. and 30° C. It should also be noted that the intensity of all spectra $I_i(\lambda)$ at their respective intersecting point $\lambda_{i/i+1}$ is greater than 20% of the respective maximum (normalized) intensity. In the present example with compounds A to E, an intensity of at least 40% of the maximum intensities is maintained for all intersecting point.

According to the invention, the half width for all dyes at least in the UV/vis region is greater than 1400 cm$^{-1}$. The half widths of the emission spectra of the compounds A to E are approximately 4250, 4400, 2850, 2890 and 1630 cm$^{-1}$, respectively.

The spectral range of the proposed standard combination can be extended to the NIR spectral range by integrating additional dyes, such as the aforedescribed merocyanin and styryl compounds having the aforedescribed general structures 6, 7, and 8. Similar selection criteria and requirements apply, whereby in the range of λ>700 nm only a minimum intensity at the overlapping points of in particular at least 12% of the maximum intensity, a half width of in particular at least 1200 cm$^{-1}$ and an anisotropy of in particular r≦0.07 are required.

To perform the spectral calibration of the fluorescence microscope, the raw emission spectra of the five (or more) aforementioned fluorescence standards A to E included in the kit are measured with the fluorescence microscope to be calibrated, with focusing performed by the focusing device(s) 24 as described above. The measurement conditions on the photoluminescence measurement device, such as slit widths, detector voltages, scan mode and speed, filters, polarizers and polarizers angles, etc., are set to those parameters typically employed in fluorescence spectra measurements or typically used for spectral correction of luminescence spectra. A baseline spectrum of the employed solvent is also measured under the same conditions as for each dye measurement. A baseline correction is then performed by subtracting the solvent spectra from the respective measured spectra, wherein the baseline-corrected measured spectra $J_i(\lambda)$ are obtained, which are also shown in the lower section of FIG. 2 as broken lines $J_A(\lambda)$ to $J_E(\lambda)$.

The measured spectra $J_i(\lambda)$ are then processed with the supplied corrected spectra $I_i(\lambda)$, which were measured with a traceable calibrated fluorescence spectrometer with a known measurement uncertainty, are corrected for baseline and spectral shifts, so that these are device-independent and traceable to the radiometric primary standard "black body" or "cryo-radiometer". First, the intersecting points (or more precisely, the intersecting wavelengths) $\lambda_{i/i+1}$ of each two spectrally sequential emission spectra are determined. Thereafter, the combination factors $\alpha_i$ are determined for each dye i by statistically averaging the overlapping spectral regions in a range ±Δλ about the respective intersecting wavelength $\lambda_{i/i+1}$ of all four adjacent spectra $I_i(\lambda)$, $I_{i+1}(\lambda)$, $J_i(\lambda)$ and $J_{i+1}(\lambda)$ according to equations 1 to 3. In this step, the partial correction functions $F_i(\lambda)$ are implicitly computed according to equation 2 by forming the quotient of the corrected spectra $I_i(\lambda)$ and the corresponding measured spectra $J_i(\lambda)$ for the individual fluorescence standards i. The curve shapes of the (unweighted) partial corrections spectra $F_A(\lambda)$ to $F_E(\lambda)$ for the standards A to E are shown in the upper section of FIG. 2.

$$\alpha_{i+1} = \frac{\sum_\lambda \left[ \frac{F_i(\lambda)}{F_{i+1}(\lambda)} \Big/ \sigma^2_{i/i+1}(\lambda) \right]}{\sum_\lambda 1/\sigma^2_{i/i+1}(\lambda)} \quad (1)$$

$$F_i(\lambda) = \frac{I_i(\lambda)}{J_i(\lambda)} \quad (2)$$

$$\sigma^2_{i/i+1}(\lambda) = \left[\frac{1}{J_i(\lambda)} + \frac{1}{J_{i+1}(\lambda)}\right] \cdot \left[\frac{F_i(\lambda)}{F_{i+1}(\lambda)}\right]^2 \quad (3)$$

The first combination factor is $\alpha_1=1$. The first summand in equation 1 for the combination factor $\alpha_{i+1}$ is preferably only determined over a predetermined optimized spectral overlap region±$\Delta\lambda_{OL}$ about the respective intersecting wavelength $\lambda_{i/i+1}$. In the present example, $\alpha_{i+1}$ is determined by statistical averaging according to equation 1 over a range of ±8 nm abutting the intersecting wavelength $\lambda_{i/i+1}$ on both sides.

The linking factors $\beta_i$ for each fluorescence standard i are then determined according to equation 4 by multiplying all the spectrally preceding combination factors $\alpha_i$. Because $\alpha_1\equiv1$, $\beta_1$ is also =1.

$$\beta_i = \prod_{k=1}^{i} \alpha_k \quad (4)$$

Finally, the total correction function $F(\lambda)$ is computed by first determining the values of the function $F(\lambda)$ in a predetermined combination region $\lambda i/i+1 \pm \Delta\lambda_{LK}$ about the respective intersecting points $\lambda_{i/i+1}$ according to equations 5 and 6. The corresponding overlapping partial correction functions $F_i(\lambda)$, weighted by $\beta_i$, are first statistically averaged in the combination region $\lambda_{i/i+1} \pm \Delta\lambda_{LK}$. In the present example, equation 5 is according to a preset execution mode of the program only applied exactly for the determined intersecting wavelengths $\lambda_{i/i+1}$, i.e., $\Delta\lambda_{LK}=0$.

$$F(\lambda) = \frac{\sum_{i=1}^{N} \beta_i \cdot F_i(\lambda)/\sigma^2(\lambda)}{\sum_{i=1}^{N} 1/\sigma^2(\lambda)} \quad (5)$$

with $$\sigma^2(\lambda) = \frac{[\beta_i F_i(\lambda)]^2}{J_i(\lambda)}. \quad (6)$$

All the other points of the correction function $F(\lambda)$, i.e., in the regions $\lambda \neq \lambda_{i/i+1} \pm \Delta\lambda_{LK}$, are preferably not averaged, but instead simply calculated with equation 7. (This is the same as summing according to equation 5 over only a single i). In other words, the total correction function $F(\lambda)$ corresponds outside the connection regions $\lambda_{i/i+1} \pm \Delta\lambda_{LK}$, in particular for all wavelengths outside the intersecting points $\lambda_{i/i+1}$, to the partial correction functions $F_i(\lambda)$, weighted by the factors $\beta_i$ determined for these functions. The obtained emission correction function $F(\lambda)$ is also shown in the upper section of FIG. 2.

$$F(\lambda)=\beta_i F_i(\lambda) \quad (7)$$

All the aforedescribed steps are automatically executed by a user-friendly computer program algorithm, which is preferably included in the kids together with the calibration system 10, the dye standards 22 and the corrected and certified fluorescence spectra $I_i(\lambda)$.

Spectra, which are measured with a measurement system calibrated in this way and under the same conditions, are spectrally corrected after subtracting the corresponding baseline spectra, by simple multiplication with the correction function $F(\lambda)$. Traceable, spectrally corrected luminescence spectra in relative intensity units are thereby obtained.

The aforedescribed example relates to generating a total correction function for the emission by using emission standards. If a set of excitation standards is measured on a luminescence measurement system in the same way and the obtained excitation spectra are accordingly processed with a dataset for the spectrally corrected (certified) excitation spectra of the fluorescence standard, then a spectral excitation correction function is obtained.

In a different embodiment of the invention, the channels 18 and the reservoirs 20 of the calibration system 10 shown in FIGS. 1A to 1D can be filled with solutions of the same fluorescence standard, but having different concentrations. The aforedescribed fluorescence standards can also be used for such purpose. The system can then be used to determine the linearity of the employed detector system in the excitation and/or emission channel of the measurement system.

| List of a reference symbols | |
|---|---|
| 10 | calibration system |
| 12 | baseplate |
| 14 | bottom side |
| 16 | topside |
| 18 | channel |
| 20 | reservoir |
| 22 | fluorescence standard |
| 24 | focusing device |
| 26 | focusing surface |
| i | sequential number of a fluorescence standard in the kit with $1 \leq i \leq N$ |
| $I_i(\lambda)$ | spectrally corrected (certified) fluorescence spectrum of the fluorescence standard i |
| $J_i(\lambda)$ | measured, baseline-corrected fluorescence spectrum |
| $F_i(\lambda)$ | partial correction function of the fluorescence standard i |
| $F(\lambda)$ | total correction function |
| $\lambda_{i/i+1}$ | overlapping wavelength of consecutive spectra of the i-th and (i + 1)-th standard |
| $\alpha_i$ | combination factor of adjacent partial correction functions |
| $\beta_i$ | linking factor |

The invention claimed is:

1. Calibration system for characterizing luminescence measurement systems, in particular spectrally resolving, wide-field and/or confocal imaging systems, comprising:
   (a) a baseplate having a thickness defined between a first side and a second side opposite to the first side, wherein the first side of the baseplate has at least one flow-through channel, wherein the at least one channel is formed as a sample chamber for the luminescence measurement system;
   (b) at least one reservoir in communication with the at least one channel and adapted to receive a liquid; and
   (c) at least one focusing device integrated into and located on the first side of the baseplate, the focusing device comprising a focusing surface adapted for setting a defined measurement beam focus of the luminescence measurement system to be calibrated, wherein the focusing surface is aligned with an interior space of the at least one flow-through channel, wherein the interior space of the at least one flow-through channel defines a plane extending longitudinally with respect to the baseplate, wherein the focusing surface is located in the plane defined by the interior space of the at least one flow-through channel, and wherein the at least one focusing device includes a highly planar lumenescing focusing surface comprising a wafer coated with a mono-layer of fluorescing nanoparticles or quantum dots.

2. The calibration system according to claim 1, wherein at least two focusing devices integrated in the baseplate are provided which are arranged at opposing marginal regions of the baseplate.

3. The calibration system according to claim 1, wherein the baseplate comprises a plurality of channels, each having at least one communicating reservoir.

4. The calibration system according to claim 1, wherein the at least one channel and/or the at least one reservoir associated with this channel is at least partially filled with at least one fluorescence standard.

5. The calibration system according to claim 1, wherein the baseplate comprises a plurality of channels and reservoirs associated with the channels, wherein the channels and/or the associated reservoirs are at least partially filled with different fluorescence standards, comprising an emission and/or excitation standard, selected from biphenyl derivates, so that their spectrally corrected fluorescence spectra in combination cover a predetermined spectral region with a predetermined minimum intensity.

6. The calibration system according to claim 5, wherein the predetermined minimum intensity of the fluorescence bands of corresponding sequential, spectrally corrected fluorescence spectra at their intersecting wavelengths in the UV/vis spectral range with $\lambda \leq 700$ nm is at least 20%, at least 25% or at least 30% of the maximum intensity of the flanking bands.

7. The calibration system according to claim 5, wherein the predetermined minimum intensity of the fluorescence bands of corresponding sequential, spectrally corrected fluorescence spectra at their intersecting wavelengths in the NIR spectral range with $\lambda \leq 700$ nm is at least 10% or approximately 15% of the maximum band intensity.

8. The calibration system according to claim 5, wherein the predetermined spectral range at least partially covers the UV/vis/NIR range and is sufficient for an emission correction from 310 to 730 nm or from 300 to 950 nm, or for an excitation correction of 280 to 600 nm or from 240 to 900 nm.

9. The calibration system according to claim 5, wherein the fluorescence standards have fluorescence bands in the UV/vis spectral range with $\lambda \leq 700$ nm with a full width at half maximum of at least 1600 cm$^{-1}$ or at least 2400 cm$^{-1}$, and in the NIR spectral range with $\lambda > 700$ nm of at least 1200 cm$^{-1}$ or at least 1400 cm$^{-1}$.

10. The calibration system according to claim 5, wherein the at least one fluorescence standard includes unstructured fluorescence bands with only a single maximum and a continuous curve form of the bands.

11. The calibration system according to claim 5, wherein the at least one fluorescence standard has a spectral separation between its absorption and emission maximum of at least 2000 cm$^{-1}$, at least 2400 cm$^{-1}$ or at least 2800 cm$^{-1}$.

12. The calibration system according to claim 1, wherein the baseplate comprises a plurality of channels and reservoirs associated with the channels, wherein the channels and/or the associated reservoirs are at least partially filled with solutions of at least one fluorescence standard in different concentrations.

13. The calibration system according to claim 1, wherein the focusing surface of the focusing device and at least one channel are located in a longitudinal plane defined by the thickness of the baseplate.

14. The calibration system according to claim 1, further comprising:
   a cover layer coated on the quantum dots.

15. The calibration system, according to claim 1, wherein, the mono-layer of quantum dots has a thickness in a range of 7 to 10 nm.

16. Kit comprising:

a calibration system comprising
- (a) a baseplate having a thickness defined between a first side and a second side located opposite to the first side, wherein the first side of the baseplate has at least one flow-through channel, wherein the at least one channel is formed as a sample chamber for the luminescence measurement system,
- (b) at least one reservoir in communication with the at least one channel and adapted to receive a liquid, and
- (c) at least one focusing device integrated into and located on the first side of the baseplate, the focusing device comprising a focusing surface adapted for setting a defined measurement beam focus of the luminescence measurement system to be calibrated by using a focusing surface, wherein the focusing surface is aligned with an interior space of the at least one flow-through channel, wherein the interior space of the at least one flow-through channel defines a plane extending longitudinally with respect to the baseplate, wherein the focusing surface is located in the plane defined by the interior space of the at least one flow-through channel, wherein the at least one focusing device includes a highly planar lumenescing focusing surface comprising a wafer coated with a mono-layer of fluorescing nanoparticles or quantum dots; and a set with different fluorescence standards.

17. The kit according to claim 16, further comprising spectrally corrected fluorescence spectra of the fluorescence standards in computer-readable form and/or information identifying an address of an Internet page for recalling the spectrally corrected fluorescence spectra.

18. The kit according to claim 16, further comprising a program algorithm for computing a total correction function for a predetermined spectral range and/or information identifying an address of an Internet page for recalling the program algorithm.

19. The kit according to claim 16, wherein
the focusing surface of the focusing device and at least one channel are located in a longitudinal plane defined by the thickness of the baseplate.

* * * * *